(12) United States Patent
Vacher et al.

(10) Patent No.: US 7,235,568 B2
(45) Date of Patent: Jun. 26, 2007

(54) 3-(CYCLOPENTEN-1-YL)-BENZYL-OR 3-(CYCLOPENTEN-1-YL)-HETEROARYL METHYL-AMINE DERIVATIVES AND USE THEREOF AS MEDICINES FOR TREATING SCHIZOPHRENIA

(75) Inventors: Bernard Vacher, Castres (FR); Stéphane Cuisiat, Castres (FR); Wouter Koek, San Antonio, TX (US); Francis Colpaert, Puylaurens (FR)

(73) Assignee: Pierre Fabre Medicament, Boulogne-Billancourt (FR)

( * ) Notice: Subject to any disclaimer, the term of this patent is extended or adjusted under 35 U.S.C. 154(b) by 0 days.

(21) Appl. No.: 11/494,697

(22) Filed: Jul. 28, 2006

(65) Prior Publication Data
US 2006/0264471 A1 Nov. 23, 2006

Related U.S. Application Data

(62) Division of application No. 10/531,587, filed as application No. PCT/FR03/03053 on Oct. 16, 2003, now Pat. No. 7,163,957.

(30) Foreign Application Priority Data

Oct. 16, 2002 (FR) .................................. 02 12854

(51) Int. Cl.
*A61K 31/443* (2006.01)
*C07D 401/12* (2006.01)
(52) U.S. Cl. .................................... 514/337; 546/284.1
(58) Field of Classification Search ............. 546/284.1; 514/337
See application file for complete search history.

(56) References Cited

U.S. PATENT DOCUMENTS 6,417,222 B1 7/2002 Vacher et al.

FOREIGN PATENT DOCUMENTS

| JP | 05-125024 | 5/1993 |
| WO | 99/51575 | 10/1999 |
| WO | 99/58527 | 11/1999 |
| WO | 00/58282 | 10/2000 |

OTHER PUBLICATIONS

Yunusaga, T. et al., "Preparation of (hetero)aryloxyalkylamine derivatives having selective affinity to serotonin (5-HT 1A) receptors", Chemical Abstracts, Oct. 25, 1993, Abstract No. 180657, vol. 119, No. 17, Chemical Abstracts Service, Columbus, OH, USA, abstract of JP05-125024.

*Primary Examiner*—Patricia L. Morris
(74) *Attorney, Agent, or Firm*—Buchanan, Ingersoll & Rooney, PC

(57) ABSTRACT

The invention provides compounds of the formula:

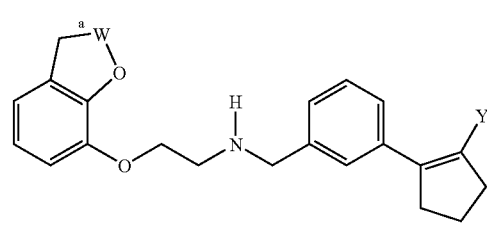

(1)

wherein (a) is a single or double bond; W is CH, $CH_2$, $CHCH_3$, $C(CH_3)_2$, $C(CH_2)_2$ or $C(CH_2)_3$; X is N; and Y is H or F, and salts, hydrates, tautomers, pure enantiomers, and enantiomeric mixtures; and a method of treating schizophrenia comprising administering same.

7 Claims, No Drawings

3-(CYCLOPENTEN-1-YL)-BENZYL-OR 3-(CYCLOPENTEN-1-YL)-HETEROARYL METHYL-AMINE DERIVATIVES AND USE THEREOF AS MEDICINES FOR TREATING SCHIZOPHRENIA

This application is a divisional application of U.S. patent application Ser. No. 10/531,587 filed Apr. 18, 2005, now U.S. Pat. No. 7,163,957, which is the U.S. national stage of International Appln. No. PCT/FR2003/003053, filed Oct. 16, 2003 which claims priority under 35 U.S.C. §119 of French Patent Appln. No. 02/12854, filed Oct. 16, 2002, said applications being incorporated by reference herein in their entireties and relied upon.

Schizophrenia is a serious and incapitating mental disease which affects more than 50 million people worldwide (Sciences 2002, 296(5598), 692–5). The mechanisms which underlie schizophrenic psychoses are complex. It appears however established that a dysfunction in the dopaminergic transmission is involved in their symptomatologies (Nature 1988, 336, 783–87; Pharmacol. Rev. 2001, 53(1), 119–33). Indeed, antagonists of the central dopaminergic receptors, in particular of the receptors of the $D_2$ subtype (e.g. haloperidol, chlorpromazine and the like) constitute a conventional and clinically effective approach to the treatment of schizophrenic psychoses, in particular of the so-called positive or productive symptoms (Nature 1976, 261, 717–19). Compounds possessing such a mechanism of action nevertheless induce side effects, not correlated with the therapeutic action, such as parkinsonian type symptoms (Pharmacotherapy 1996, 16, 160), tardive dyskinesia, endocrine disorders and the like (Drug Metab. Dispos. 1997, 25(6), 675–84). Another class of so-called atypical antipsychotic agents was introduced more recently (ID 2002, 3(7), 1073–80). In terms of therapeutic advantages, the advantage of these novel agents compared with the conventional agents lies in:
- a lower propensity to causing side effects of a neurological order, in particular extra-pyramidal effects (J. Clin. Psychiatry 2000, 61(S3), 10–5);
- an increased antideficiency activity (CNS Drugs 2002, 16(4), 249–61);
- a greater efficacy in certain refractory forms of schizophrenia (CNS Drugs 2002, 16(7), 473–84).

These atypical compounds (e.g. clozapine, risperidone, olanzapine and the like) act in general both as dopaminergic and serotoninergic antagonists, in particular at the level of the 5-$HT_2$ type receptors (Rsychopharmacol. Bull. 1989, 25, 390–92; Psychopharmacology 1993, 112, S40–S54). Each of these medicaments possesses nevertheless a different affinity profile not only at the level of the subtypes of dopaminergic and serotoninergic receptors, but also at the level of the muscarinic, adrenergic and histaminic receptors. Thus, an affinity profile characteristic of an "atypical" status does not appear to emerge.

It is evident, nevertheless, from several clinical studies (Br. Med. J. 2000, 321, 1360–61 and 1371–76) that in general:
- the atypical agents are no more effective than the so-called conventional agents, at least from the point of view of the positive (or productive) symptoms; the impact on the deficiency (or negative) syndromes being more difficult to objectify in human clinical medicine;
- the atypical agents exhibit better neurological tolerance than conventional agents, but induce moreover side effects which are specific to them (e.g. weight gain, diabetes, sexual disorders, hematological and/or cardiac toxicity ad the like); some of these side effects being as serious as the extrapyramidal effects sometimes associated with treatments with conventional agents (Br. Med. J. 2002, 325, 243–5).

Overall, the existing therapeutic approaches for the treatment of schizophrenic psychoses are therefore not completely satisfactory (J. Med. Chem. 2001, 44(4) 477–501). The discovery of novel more effective and better tolerated treatments is therefore highly desirable.

It has been shown in animals that the 5-$HT1_A$ antagonists are, inter alia, capable of combating catelepsy (J. Neural Transm. 1991, 83(1–2), 43–53; J. Pharmacol. Exp. Ther. 1993, 265(1), 207–17; Eur. J. Pharmacol. 1998, 356, 189–92) and of attenuating the increase in the plasma level of prolactin (J. Pharmacol. Exp. Ther. 1989, 249, 23641), induced by $D_2$ antagonists. 5-$HT1_A$ agonists also have in their capacity to increase the release of dopamine and acetylcholine in the prefrontal cortex (Brain Res. 2002, 939, 34–42), properties which conventional agents do not possess and which are assumed to contribute to the antideficiency activity of the so-called "atypical" agents (J. Psychopharmacol. 2001, 15(1) 37–46). Finally, the anxiolytic and antidepressant effects of the 5-$HT1_A$ agonists constitute an advantage during the treatment of schizophrenic psychoses. The combination, in the same medicament, of an activity of the $D_2$ receptor antagonist type and of the 5-$HT1_A$ subtype receptor agonist type is therefore, in theory, highly desirable since it would confer both a broader activity spectrum (e.g. positive symptoms, antideficiency activity, antidepressant activity and the like) and a better tolerance than conventional agents (e.g. extrapyramidal effects) and than most atypical agents. Given the potential therapeutic benefit represented by a $D_2$ antagonist and 5-$HT1_A$ agonist combination, numerous compounds having such a profile are described in the literature (J. Pharmacol. Exp. Ther. 2000, 295(3), 853–61). There may be mentioned, by way of example, arylpiperazine derivatives (e.g., Bioorg. Med. Chem. Lett. 2001, 11, 2345–49; J. Med. Chem. 2001, 44, 186–97; Biorg. Med. Chem. Lett. 1999, 9, 1679–82; Pharmazie 2001, 56, 803–07; J. Med. Chem. 1998, 41, 2010–18; Pharmazie, 1998, 53, 438–41; Arzneim-Forsch. 1997, 47, 239–43; Med. Chem. Res. 1997, 7, 76–86; Pharmzie 1997, 52, 423–8; J. Med. Chem. 1994, 37, 99–104; DE 10043659; WO 0216354; WO 9811068; WO 9703067; J. Med. Chem. 1992, 35, 552–58; J. Med. Chem. 1995, 38, 1498–20; WO 9955672; U.S. Pat. No. 6,310,066; J. Med. Chem. 1998, 41, 760–71 and WO 09711070; Bioorg. Med. Chem. Lett. 2001, 11, 2345–49; Drug of the Future 2001, 26, 128–32; Exp. Opin. Ther. Patents 1998, 8, 737–40 and EP 900792; EP 770066; WO 9736893; WO 9711070 and J. Med. Chem. 1998, 41, 760–71; WO 9818797; WO 0168063); aminotetralin derivatives (e.g. Bioorg, Med. Chem. Lett. 1999, 9, 1583–86; Biorg. Med. Chem. Lett. 1999, 7, 1263–71 and 2541–48; Bioorg. Med. Chem. Lett. 1999, 7, 2541–48; J. Med. Chem. 1993, 36, 1053–68); benzodioxane derivatives (e.g., EP 707007; WO 0172741; WO 9840386; WO 9829415; WO 9723485; WO 9507274 and J. Med. Chem. 1999, 42, 3342–55; WO 9717343; EP 669331); aryloxyethylamine derivatives (e.g., WO 0198293; WO 9808817; U.S. Pat. No. 5,958,965; WO 9951576).

However, despite the abundance of compounds described as $D_2$ antagonists and 5-$HT1_A$ agonists, only one remains clinically available (i.e. nemonapride: RN 75272-39-8) and three are reported as being under active development in neuroleptic indication (PJB Publications Ltd. 2002) i.e. SSR-181507 (Sanofi-Synthelabo), bifeprunox and SLV-313 (Solvay). The contrast between the number of candidates and the number of compounds in clinical medicine illustrates, inter alia, the difficulties in obtaining additional effects from the concomitant action of two distinct systems by means of a single chemical entity. In this regard, the Applicant has discovered that several compounds derived from (3-(cyclopenten-1-yl)-[benzyl or pyrid-3-ylmethyl])-(2-aryloxyethyl)amine selectively interact with the dopaminergic receptors of the $D_2/D_3$ subtypes and the serotoninergic receptors of the 5-HT$1_A$ subtype at the level of which they behave as antagonists and agonists, respectively. As conventional agents, and unlike the so-called "atypical" compounds, the compounds of the invention have the advantage, in vivo, of effectively blocking the $D_2$ type receptors and therefore of being potentially active in the treatment of the productive symptoms of schizophrenia. However, unlike the conventional agents and certain atypical agents, the compounds of the invention do not cause catalepsy in animals even at doses much higher than the pharmacological doses. The induction of catalepsy in animals is known as being representative of the extrapyramidal effects which manifest themselves in humans. The activity profile of the compounds of the invention is therefore, in this regard, quite remarkable. As such, the compounds of the invention are therefore potentially useful for the treatment of schizophrenic psychoses for which a great therapeutic need exists. The closest state of the art is represented by the compounds described in patents JP 05255302 and JP 05125024 of formula:

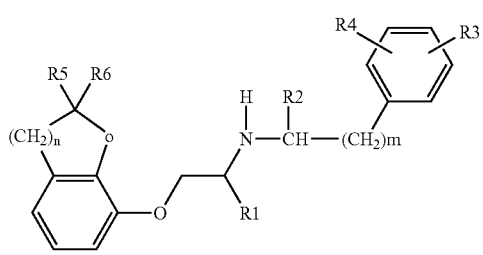

in which:

R1, R2, R5 and R6 may be a hydrogen atom or a simple alkyl group;

R3 and R4 represent, inter alia, a hydrogen atom or a simple alkyl group;

m is between 1 and 5;

n is between 1 and 4.

The compounds in question are claimed as being selective ligands of the 5-HT$1_A$ receptors which are useful for the treatment of disorders affecting the central nervous system.

U.S. Pat. No. 6,121,307 and WO 9951575 claim N-[(aryloxy)ethyl]indoylalkylamines of formula:

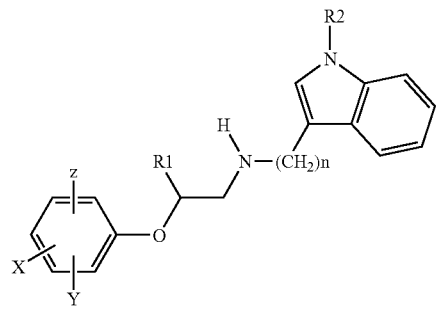

in which

R1 may be a hydrogen atom;

X and Y can form a heterocycle of the furanyl or dihydrofuranyl type;

n is between 2 and 5;

as active agents at the level of the serotoninergic system, in particular on the 5-HT$1_A$ receptors, which are useful in the treatment of depression.

The compounds of the invention therefore differ from the derivatives of the prior art both in their mechanism of action and in their chemical formula. For example, the fragment [3-cyclopenten-1-ylbenzylamino] only appears in the derivatives of the 4-(1-cyclopenten-1-yl)-2-[(dialkylamino)methyl]phenol type used as complexing agents (Izv. Vyssh. Uchebn. Zaved., Khim. Tekhnol. 1980, 23(4), 406–11). The major benefit of the compounds of the invention therefore lies in their complementary action, or even in some synergistic cases, at the level of the serotoninergic and dopaminergic systems. Indeed, we show in vivo that the dose-effect curve (i.e. normalization of the stereotypisms which is due to the activation of the dopaminergic receptors) of certain compounds of the invention is moved to the right in the presence of the selective 5-HT$1_A$ antagonist WAY-100635 (RN 162760-96-5). Conversely, these same products become highly cataleptigenic in the presence of WAY-100635.

This synergy of activity, which is unexpected in the light of the results for the compounds of the prior art claiming a similar, mixed mechanism of action (Psychopharmacol. 1999, 144(1), 20–29) opens novel therapeutic perspectives in human clinical medicine in a field for which the existing medicaments are not totally satisfactory.

More specifically, the subject of the present invention is novel derivatives of the [(benzofuranyl-7-oxy)ethyl]-[(cyclopenten-1-yl)-{aryl or heteroaryl}-methyl]amine type which, in the form of a base, corresponds to general formula (1):

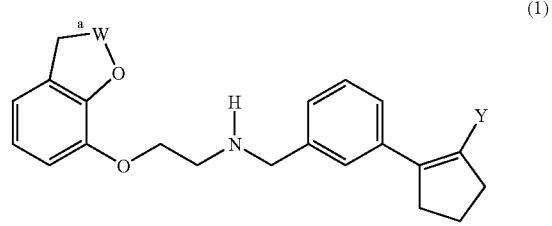

in which:
(a) represents a single bond or a double bond;
W represents a CH, CH$_2$, CHCH$_3$, CCH$_3$ or C(CH$_3$)$_2$ group, a C(CH$_2$)$_2$ group (i.e. a carbon atom bearing two methylene groups linked together so as to form a spiro-cyclopropane unit) or a C(CH$_2$)$_3$ group (i.e. a carbon atom bearing two methylene groups linked to another methylene group so as to form a spiro-cyclobutane unit) with the proviso, however, that when (a) is a double bond, then W exclusively represents a CH or CCH$_3$ group, and that when (a) is a single bond, then W exclusively represents a CH$_2$, CHCH$_3$, C(CH$_3$)$_2$, C(CH$_2$)$_2$ or C(CH$_2$)$_3$ group;
X is a carbon atom bearing a hydrogen atom (CH) or a nitrogen atom;
Y is a hydrogen atom or a fluorine atom;

their addition salts and optionally the hydrates of the addition salts with pharmaceutically acceptable inorganic acids or organic acids and their tautomeric forms, the pure enantiomers and mixtures of racemic or nonracemic enantiomers.

Some compounds of the invention contain an asymmetric carbon atom in their structure. Consequently, they exist in the form of enantiomers. The invention relates to both each pure enantiomer, that is to say combined with less than 5% of the other enantiomer, and their mixture in any proportions. The compounds of the invention may therefore be used as pure enantiomers or racemic or nonracemic mixtures.

The invention finally extends to the process for preparing the derivatives of general formula (1). The derivatives of general formula (1) may be obtained by the process described in Scheme A.

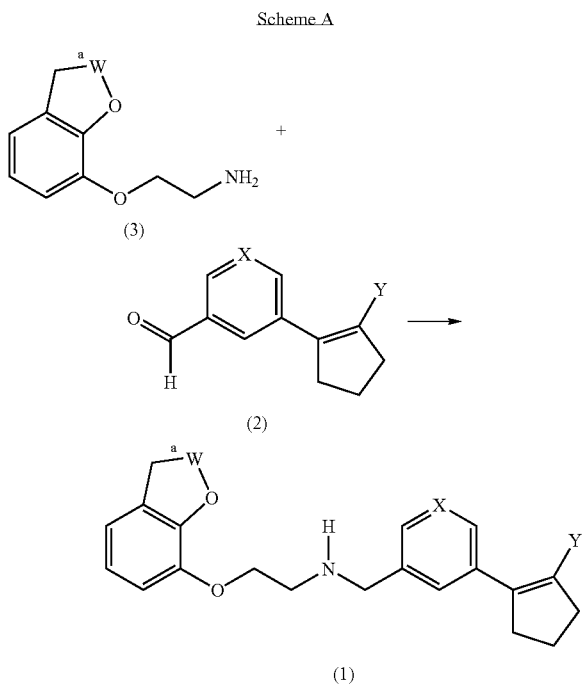

Scheme A

The compound of formula (1) is prepared by a conventional reductive amination reaction between the aldehyde of formula (2), in which X and Y have the same meaning as above, and the primary amine of formula (3), in which (a) and W have the same meaning as above. The expression "a conventional reductive amination reaction" means that the aldehyde of formula (2) and the primary amine of formula (3) are reacted in an appropriate solvent and that the mixture of the reagents (2) and (3) is then subjected to the reducing agent according to a method well known to the organic chemist.

The compounds of formula (1) are purified according to one or more methods chosen from crystallization and/or liquid phase chromatography techniques. They may then be, if desired, salified by means of a pharmaceutically acceptable acid.

The preparation of the aldehydes of formula (2) depends on the nature of the groups X and Y. Thus, the preparation of the aldehyde (2a) in which X represents a carbon atom bearing a hydrogen atom (CH) and Y is a hydrogen atom is described in scheme B.

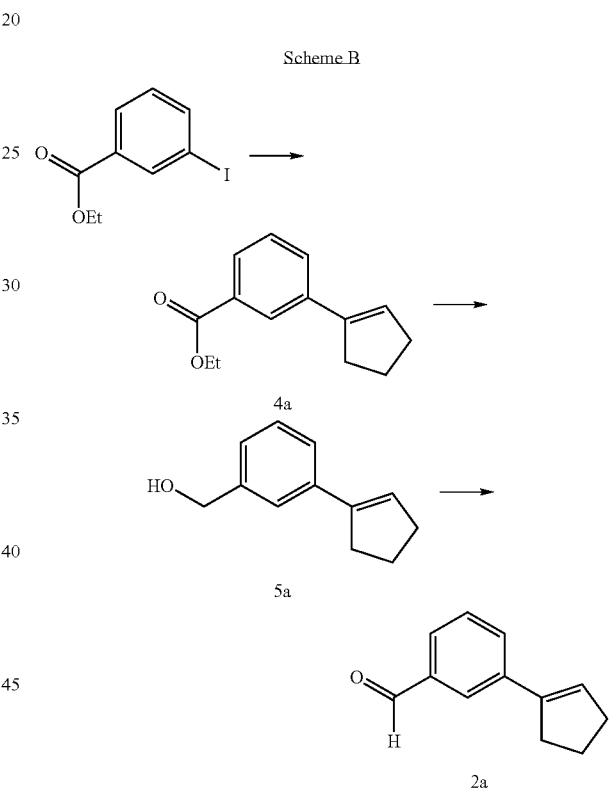

Scheme B

The ethyl 3-cyclopenten-1-ylbenzoate of formula (4a) is directly obtained from ethyl 3-iodobenzoate and cyclopentene, which are commercially available, by means of a Heck reaction catalyzed by tris(dibenzylideneacetone)dipalladium (RN 52409-22-0). The reduction of the ester functional group of the compound of formula (4a) by means of a hydride-donating agent such as, for example, lithium aluminum hydride leads to the alcohol of formula (5a). The oxidation of the primary alcohol functional group to the expected aldehyde of formula (2a) is then carried out by means of manganese dioxide in chloroform in the hot state.

The preparation of the aldehyde (2b) in which X represents a (CH) group and Y represents a fluorine atom is described in Scheme C.

Scheme C

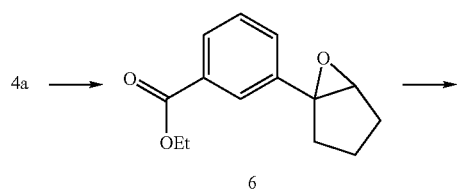

6

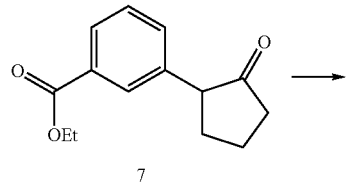

7

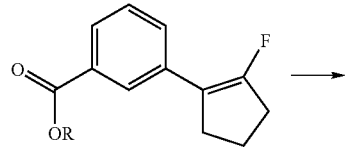

4b

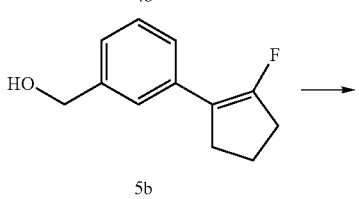

5b

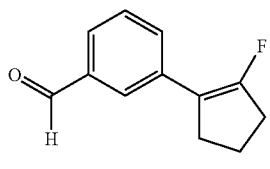

2b

Scheme D

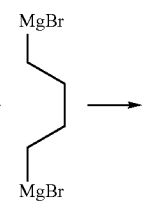

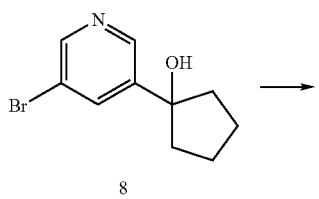

8

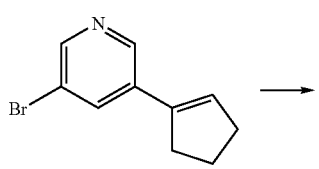

9

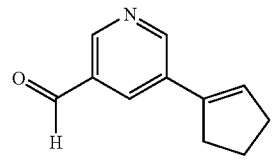

2c

Scheme C

The ethyl 3-(2-oxocyclopentyl)benzoate of formula (7) is obtained by rearrangement (J. Org. Chem 1996, 61(5), 1877–79 and Synth. Commun. 1990, 20(12), 1751–56) of the epoxide of formula (6), which is itself prepared by epoxidation of the double bond of the intermediate (4a, Scheme B) by means of an organic peracid such as, for example, m-chloroperbenzoic acid. The conversion of the ketone functional group of the compound of formula (7) to a gem-difluoro functional group, followed by the removal of HF in a basic medium (Tetrahedron 1990, 46(12), 4255–60), gives the derivative of formula (4b). The reduction of the ester functional group of the compound (4b) to a primary alcohol, and then its oxidation according to a sequence similar to that described above (cf. Scheme B), leads to the expected aldehyde of formula (2b).

The preparation of the aldehyde (2c) in which X represents a nitrogen atom and Y is a hydrogen atom is described in Scheme D.

Scheme D

The addition of 1,4-bis(bromomagnesio)butane (RN 23708-47-6) to the methyl ester of 5-bromonicotinic acid (RN 29681-44-5), which is carried out according to a protocol similar to that described in Eur. J. Med. Chem. 1991, 26, 563, leads to 1-(5-bromopyridin-3-yl)cyclopentanol of formula (8). A dehydration reaction gives the unsaturated derivative (9) which may then be converted to the expected aldehyde (2c) by applying a method similar to that described in Tetrahedron Lett. 2002, 43, 4285–87.

The primary amines of formula (3), in which W and (a) are as defined above, may be prepared according to a method similar to those described in patents U.S. Pat. No. 6,121,307; WO 0058282 and WO 0032557 (Scheme E):

Scheme E

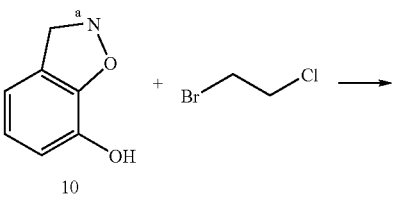

10

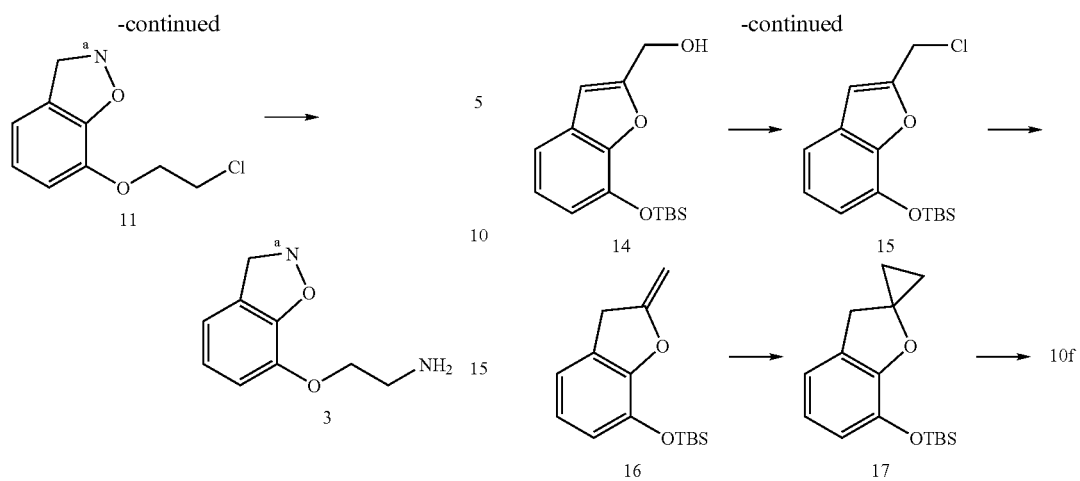

thus, the monoalkylation of a suitably substituted hydroxylated derivative (10), by means of 1-bromo-2-chloroethane, which is commercially available, leads to the ether of formula (11). The nitrogen atom is then introduced by substitution of the chlorine atom of compound (11) by means of an appropriate reagent such as for example sodium azide or potassium phthalimide. The primary amine functional group is then released either by reducing the azido functional group or by hydrazinolysis of the phthalimido functional group to give the corresponding primary amines (3).

The hydroxylated derivatives of formula (10), which are used as raw materials in the synthesis of the compounds of formula (11), are obtained in the following manner:

- the compound (10a) in which W is a $C(CH_3)_2$ group and (a) represents a single bond is commercially available (RN 1563-38-8);
- the compound (10b) in which W is a $CHCH_3$ group and (a) represents a single bond is described in patents U.S. Pat. No. 3,547,955; WO 8700840 and WO 9630367;
- the compound (10c) in which W is a CH group and (a) represents a double bond is prepared according to patent U.S. Pat. No. 6,121,307;
- the compound (10d) in which W is a $CCH_3$ group and (a) represents a double bond is prepared according to the method described in Tetrahedron 1996, 52(28), 9499–9508;
- the compound (10e) in which W is a $CH_2$ group and (a) represents a single bond is prepared according to French patent filing No.: 01 03877;
- the compound (10f) in which W is a $C(CH_2)_2$ group and (a) represents a single bond is prepared according to the process illustrated in Scheme F below.

Scheme F

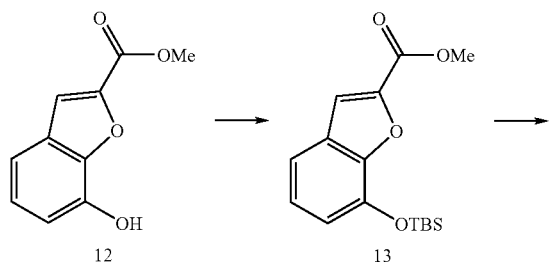

Scheme F

The hydroxyl group of the compound of formula (12), EP 50957, is first of all protected in the form of a silylated ether (in Scheme F, the abbreviation TBS means tert-butyldimethylsilyl). The ester functional group of the compound of formula (13) may then be reduced to a primary alcohol by means of a hydride-donating agent (J. Pharm. Pharmacol. 1999, 51(4), 427–34). After converting the hydroxyl group of compound (14) to a chlorine atom, a reductive rearrangement reaction (Tetrahedron Lett. 2001, 42, 939–41) makes it possible to obtain an exo-methylene derivative (16). A cyclopropanation reaction, which is carried out according to J. Org. Chem. 1992, 57(19), 5271–76, provides the spiropropane compound (17) which is then deprotected to give the expected compound (10f).

The subject of the invention is also the pharmaceutical compositions containing, as active ingredient, at least one of the derivatives of general formula (1) or one of its salts or hydrates of its salts in combination with one or more inert carriers or other pharmaceutically acceptable vehicles.

The pharmaceutical compositions according to the invention may be, by way of example, compounds which can be administered orally, nasally, sublingually, rectally or parenterally. By way of example of compositions which can be administered orally, there may be mentioned tablets, gelatin capsules, granules, powders and oral solutions or suspensions. The formulations appropriate for the chosen form for administration are known and described for example in: Remington, The Science and Practice of Pharmacy, 19th edition, 1995, Mack Publishing Company.

The effective dose of a compound of the invention varies according to numerous parameters such as for example the chosen route of administration, the weight, age, gender, state of progression of the pathology to be treated and the sensitivity of the individual to be treated. Consequently, the optimum dosage will have to be determined according to the parameters which are judged to be relevant by the specialist in the field. Although the effective doses of a compound of the invention can vary in large proportions, the daily doses could be between 0.001 mg and 100 mg per kg of bodyweight of the individual to be treated. A daily dose of a compound of the invention of between 0.010 mg and 50 mg per kg of bodyweight of the individual to be treated is however preferred.

The pharmaceutical compositions according to the invention are useful in the treatment of schizophrenic psychoses.

EXAMPLES

The following examples illustrate the invention without however limiting its scope.

In the examples below:

(i) The progress of the reactions is monitored by thin-layer chromatography (TLC) and consequently the reaction times are only mentioned as a guide.

(ii) The various crystalline forms can give different melting points; the melting points reported in the present application are those of the products prepared according to the method described and are not corrected.

(iii) The structure of the products obtained according to the invention is confirmed by nuclear magnetic resonance (NMR) and infrared (IR) spectra, and percentage analysis; the purity of the final products is checked by TLC.

(iv) The NMR spectra are recorded in the solvent indicated. The chemical shifts (δ) are expressed in part per million (ppm) relative to the tetramethylsilane. The multiplicity of the signals is indicated by: s, singlet; d, doublet; t, triplet; q, quadruplet; m, multiplet; b, broad.

(v) The various symbols for the units have their usual meaning: mg (milligram); g (gram); ml (milliliter); ° C. (degree Celsius); mmol (millimol); nmol (nanomol); cm (centimeter).

(vi) The abbreviations have the following meaning: m.p. (melting point); b.p. (boiling point).

(vii) In the present application, the pressure values are given in millibar; the expression "room temperature" is understood to mean a temperature of between 20° C. and 25° C.

Example 1

Ethyl 3-cyclopenten-1-ylbenzoate (4a)

The following are successively introduced into a round-bottomed flask: 7 g of ethyl 3-iodobenzoate (25 mmol), 11.2 ml of cyclopentene (127 mmol), 21 ml of ethanol, 1.16 g of $Pd_2dba_3$ complex (1.27 mmol), 8.8 g of potassium carbonate (63 mmol) and 8.17 g of $nBu_4NBr$ (25 mmol). The medium is heated at 80° C. for 16 hours and then the black mixture is filtered on celite. The precipitate is washed with ethyl acetate. The filtrate is washed with water and then with a saturated aqueous sodium chloride solution, dried over sodium sulfate, filtered and then concentrated under reduced pressure. The title product, which is isolated by bulb to bulb distillation (5.2 g), is obtained in the form of a pale yellow oil.

$^1$H NMR ($CDCl_3$): δ 1.39 (t, J=7.1 Hz, 3H); 2.04 (m, 2H); 2.54 (m, 2H); 2.73 (m, 2H); 4.34 (q, J=7.1 Hz, 2H); 6.27 (s, 1H); 7.35 (t, J=7.7 Hz, 1H); 7.61 (d, J=7.8 Hz, 1H); 7.88 (d, J=7.8 Hz, 1H); 8.06 (s, 1H).

Example 2

(3-Cyclopenten-1-ylphenyl)methanol (5a)

A solution of ethyl 3-cyclopent-1-ylbenzoate (4a) (2.5 g, 12 mmol) in ether (25 ml) is added dropwise to a suspension at 0° C. of $LiAlH_4$ (0.57 g, 15 mmol) in ethyl ether (30 ml). The mixture is stirred overnight at room temperature. The reaction mixture is cooled to 0° C. and then 4.1 ml of a 10% aqueous sodium hydroxide solution are added dropwise. The white precipitate formed is filtered under vacuum, the solid washed with ether and then the filtrate concentrated under reduced pressure. The residue is purified by flash chromatography on silica gel (cyclohexane/ethyl acetate: 90/10). The title product (1.35 g) is obtained in the form of a colorless oil.

$^1$H NMR ($CDCl_3$): δ 2.02 (m, 2H); 2.53 (m, 2H); 2.72 (m, 2H); 3.74 (s, 1H); 4.68 (d, J=6.0 Hz, 2H); 6.21 (s, 1H); 7.20 (d, J=7.4 Hz, 1H); 7.29 (t, J=7.6 Hz, 1H); 7.38 (d, J=7.7 Hz, 1H); 7.44 (s, 1H).

Example 3

3-Cyclopenten-1-ylbenzaldehyde (2a)

1.35 g (8 mmol) of (3-cyclopenten-1-ylphenyl)methanol (5a) and 80 ml of chloroform are introduced into a round-bottomed flask. 6.8 g of $MnO_2$ are then added and the suspension is heated at 60° C. for 2 hours. The mixture is filtered in the hot state, the precipitate washed with chloroform and then the filtrate concentrated under reduced pressure. The title product (1.05 g) is obtained in the form of a yellow oil which is used in the next step without further purification.

$^1$H NMR ($CDCl_3$): δ 2.06 (m, 2H); 2.57 (m, 2H); 2.72 (m, 2H); 6.30 (s, 1H); 7.49 (t, J=7.6 Hz, 1H); 7.71 (m, 2H); 7.91 (s, 1H); 10.02 (s, 1H).

Example 4

Ethyl 3-(6-oxabicyclo[3.1.0]hex-1-yl)-benzoate (6)

5 g (23 mmol) of ethyl 3-cyclopent-1-ylbenzoate (4a) and 100 ml of methylene chloride are introduced into a round-bottomed flask. The solution is cooled to 0° C. and 9 g (28 mmol) of meta-chloroperbenzoic acid are added in portions. The mixture is stirred for 30 minutes at 0° C. and then for 4 hours at room temperature. The mixture is filtered. The filtrate is successively washed with a saturated aqueous sodium thiosulfate solution, a saturated aqueous sodium bicarbonate solution and then with a saturated aqueous sodium chloride solution. The organic phase is dried over $Na_2SO_4$, filtered and concentrated under reduced pressure. The residue is purified by flash chromatography on silica gel (cyclohexane/ethyl acetate: 95:5). The title product is obtained in the form of a colorless oil (4.8 g).

$^1$H NMR ($CDCl_3$): δ 1.40 (t, J=7.2 Hz, 3H); 1.62 (m, 1H); 1.78 (m, 2H); 2.13 (m, 1H); 2.24 (m, 2H); 3.57 (s, 1H); 4.38 (q, J=7.2 Hz, 2H); 7.41 (t, J=7.7 Hz, 1H); 7.56 (d, J=7.7 Hz, 1H); 7.96 (d, J=7.7 Hz, 1H); 8.06 (s, 1H).

Example 5

Ethyl 3-(2-oxocyclopentyl)benzoate (7)

4 g (17.2 mmol) of ethyl 3-(6-oxabicyclo[3.1.0]hex-1-yl) benzoate (6) and 50 ml of methylene chloride are introduced into a round-bottomed flask. The mixture is cooled to 0° C. and then 2.2 ml (17.2 mmol) of $BF_3.Et_2O$ are added dropwise. The reaction mixture is stirred at 0° C. for 1 hour and then 25 ml of a saturated aqueous sodium bicarbonate solution are added. The mixture is separated by settling and the aqueous phase extracted with methylene chloride. The combined organic phases are dried over $MgSO_4$, filtered and concentrated under reduced pressure. The residue is purified by flash chromatography on silica gel (cyclohexane/ethyl acetate: 80/20). The title product is obtained in the form of a pale yellow oil (3.4 g).

¹H NMR (CDCl₃): δ 1.38 (t, J=7.2 Hz, 3H); 1.98 (m, 1H); 2.17 (m, 2H); 2.31 (m, 1H); 2.51 (m, 2H); 3.38 (dd, J=11.2; 8.6 Hz, 1H); 4.36 (q, J=7.2 Hz, 2H); 7.39 (m, 2H); 7.86 (s, 1H), 7.93 (m, 1H).

Example 6

Alkyl 3-(2-fluorocyclopenten-1-yl)benzoate (4b)

4 g of ethyl 3-(2-oxocyclopentyl)benzoate (7) (17.2 mmol) and 8 ml of toluene are added to a round-bottomed flask. 9 ml of DAST (69 mmol) are then added dropwise and the mixture is heated at 60° C. for 16 hours. The solution is poured into an ice/sodium bicarbonate mixture and then the mixture is extracted with methylene chloride. The organic phase is washed with water, with an aqueous saturated sodium chloride solution, dried over sodium sulfate, filtered and then concentrated under reduced pressure. The residue is purified by filtration on silica gel (cyclohexane/ethyl acetate: 90/10). The brown oil obtained (2.9 g) is taken up in tetrahydrofuran (50 ml) and the solution cooled to −15° C. 34 ml of potassium tert-butoxide (1M in tetrahydrofuran, 34 mmol) are slowly added and the mixture is stirred at −15° C. for 3 hours. The mixture is poured into water, extracted with ether and then the combined organic phases are washed with a saturated aqueous sodium chloride solution, dried over MgSO₄ and concentrated under reduced pressure. A brown oil (2.5 g) is obtained which is used in the next step without further purification.

Example 7

3-(2-Fluorocyclopenten-1-yl)methanol (5b)

A solution of the derivative (4b) (2 g, 9 mmol) in ethyl ether is added dropwise to a suspension of LiAlH₄ (0.8 g, 21 mmol) in ether (20 ml) kept at 0° C. The reaction mixture is slowly heated to room temperature and then stirred for 16 hours. A 10% aqueous sodium hydroxide solution (4 ml) is then added at 0° C. The white precipitate formed is filtered under vacuum, washed with ether and then the filtrate concentrated under reduced pressure. The residue is purified by flash chromatography on silica gel (cyclohexane/ethyl acetate: 70/30). The title product is obtained in the form of a pale yellow oil (1.62 g).

¹H NMR (CDCl₃): δ 1.58 (s, 1H); 2.02 (m, 2H); 2.70 (m, 4H); 4.70 (s, 2H); 7.23 (m, 1H); 7.34 (t, J=7.7 Hz, 1H); 7.39 (m, 1H); 7.45 (m, 1H).

Example 8

3-(2-Fluorocyclopenten-1-yl)benzaldehyde (2b)

A suspension of MnO₂ (1.6 g) and 3-(2-fluorocyclopenten-1-yl)methanol (5b) (0.64 g, 3.3 mmol) in 15 ml of chloroform is heated at 60° C. for 5 hours. The mixture is filtered in the hot state, the precipitate is washed with chloroform and then the filtrate concentrated under reduced pressure. The residue is purified by flash chromatography on silica gel (cyclohexane/ethyl acetate: 80/20). The title product is obtained in the form of a and a yellow oil is obtained (0.56 g).

¹H NMR (CDCl₃): δ 2.04 (m, 2H); 2.74 (m, 4H); 7.51 (t, J=7.7 Hz, 1H); 7.73 (d, J=7.6 Hz, 1H); 7.93 (s, 1H); 7.79 (d, J=7.7 Hz, 1H); 10.02 (s, 1H).

Example 9

1-(5-Bromopyridin-3-yl)cyclopentanol (8)

A few drops of 1,4-dibromobutane and 25 ml of tetrahydrofuran are added to a round-bottomed flask containing 2.25 g of magnesium chips (92.6 mmol) and an iodine crystal. The mixture is heated at 65° C. until decolorization is obtained and then a solution of 1, 4-dibromobutane (10 g, 46.3 mmol) in 50 ml of tetrahydrofuran is added dropwise. The reaction mixture is heated at 65° C. for 4 hours and then cooled to 0° C. A solution of ethyl 2-bromonicotinate (10 g, 46.3 mmol) in 60 ml of tetrahydrofuran is then added. The reaction mixture is cooled to room temperature and stirred for 16 hours. The reaction mixture is slowly poured at 0° C. into a saturated aqueous ammonium chloride solution and then the medium is extracted with ethyl acetate. The organic phase is washed with water and then with a saturated aqueous sodium chloride solution, dried over sodium sulfate, filtered and concentrated under reduced pressure. The residue is purified by flash chromatography on silica gel (cyclohexane/ethyl acetate: 70/30). The title product (3.6 g) is obtained in the form of a white solid.

m.p.=74° C. ¹H NMR (CDCl₃): δ 1.76 (m, 2H); 1.87 (m, 6H); 2.73 (m, 2H); 3.93 (s, 1H); 7.15 (d, J=5.0 Hz, 1H); 8.38 (d, J=5.0 Hz, 1H); 8.64 (s, 1H).

Example 10

3-Bromo-5-cyclopenten-1-ylpyridine (9)

A solution of 1-(5-bromopyridin-3-yl)cyclopentanol (8) (1.7 g, 11.3 mmol) in 50 ml of toluene containing 5 ml of concentrated hydrochloric acid is heated at 120° C. for 12 hours with continuous carrying away of the water formed. The mixture is then poured into a saturated aqueous sodium bicarbonate solution and extracted with ethyl acetate. The combined organic phases are washed with water and then with a saturated aqueous sodium chloride solution, dried over sodium sulfate, filtered and concentrated under reduced pressure. The residue is purified by flash chromatography on silica gel (cyclohexane/ethyl acetate: 60/40). The title product is obtained in the form of a beige solid (1.65 g).

m.p.=43° C. ¹H NMR (CDCl₃): δ 2.05 (m, 2H); 2.57 (m, 2H); 2.72 (m, 2H); 6.31 (s, 1H); 7.82 (m, 1H); 8.49 (d, J=2.0 Hz, 1H); 8.59 (d, J=2.0 Hz, 1H).

Example 11

5-Cyclopenten-1-ylpyridine-3-carboxaldehyde (2c)

A solution of 3-bromo-5-cyclopenten-1-ylpyridine (9) (1 g, 4.5 mmol) in 25 ml of ether is added to a solution of n-butyllithium (1.6M in hexane, 4.2 ml, 6.7 mmol) in 25 ml of ether kept at −60° C. The reaction mixture is stirred for 2 h 30 min at −60° C. and then 1.4 ml of 4-morpholinecarboxaldehyde (13.4 mmol) are added. The reaction is stirred for 1 hour at −60° C. and then poured into water, the organic phase is washed with a saturated aqueous sodium chloride solution, dried over sodium sulfate, filtered and concentrated under reduced pressure. The residue is purified by flash chromatography on silica gel (cyclohexane/ethyl acetate: 80/20). The title product is obtained in the form of a beige solid (0.38 g).

m.p.=50° C. ¹H NMR (CDCl₃): δ 2.10 (m, 2H); 2.61 (m, 2H); 2.72 (m, 2H); 6.49 (s, 1H); 8.32 (s, 1H); 8.89 (s, 1H); 8.93 (s, 1H); 10.10 (s, 1H).

Example 12

7-(tert-Butyldimethylsilanyloxy)benzofuran-2-methoxycarbonyl (13)

1.61 g of tert-butyldimethylsilane (10.7 mmol) and 0.73 g of imidazole (10.7 mmol) are added to a solution of 7-hydroxybenzofuran-2-methoxycarbonyl (1.96 g, 10.2 mmol) in dimethylformamide (10 ml), kept at 0° C. The mixture is stirred for 16 hours at room temperature. The mixture is then poured into water, extracted with ethyl acetate and the combined organic phases are washed with a saturated aqueous sodium chloride solution, dried over $MgSO_4$ and concentrated under reduced pressure. The residue is purified by flash chromatography on silica gel (cyclohexane/ethyl acetate: 95/5). The title product is obtained in the form of a pale yellow oil (3.1 g).

$^1$H NMR (CDCl3): δ 0.27 (s, 6H); 1.05 (s, 9H); 3.95 (s, 3H); 6.92 (d, J=7.7 Hz, 1H); 7.14 (t, J=7.8 Hz, 1H); 7.25 (d, J=7.8 Hz, 1H); 7.49 (s, 1H).

Example 13

[7-(tert-Butyldimethylsilanyloxy)benzofuran-2-yl]methanol (14)

A solution of $LiAlH_4$ (8.4 ml, 8.4 mmol) in ethyl ether (1.0M) is added dropwise to a solution of 7-(tert-butyldimethylsilanyloxy)benzofuran-2-methoxycarbonyl (13) (2.15 g, 7 mmol) in ether (14 ml), kept at 0° C. The mixture is stirred for 18 hours at room temperature and then cooled to 0° C. and treated dropwise with a 10% aqueous sodium hydroxide solution (1.6 ml). The precipitate formed is filtered under vacuum and washed with ether. The filtrate is concentrated under reduced pressure to give a colorless liquid (1.8 g) used in the next step without further purification.

$^1$H NMR (CDCl$_3$): δ 0.24 (s, 6H); 1.04 (s, 9H); 1.85 (t, J=6.4 Hz, 1H); 4.76 (d, J=6.0 Hz, 2H); 6.64 (s, 1H); 6.76 (d, J=7.7 Hz, 1H); 7.04 (t, J=7.7 Hz, 1H); 7.14 (d, J=7.7 Hz, 1H).

Example 14 tert-Butyldimethyl-(2-chloromethylbenzofuran-7-yloxy)silane (15)

2.5 g (9.5 mmol) of triphenylphosphine and 0.92 ml (9.5 mmol) of carbon tetrachloride are added to a solution of [7-(tert-butyldimethylsilanyloxy)-benzofuran-2-yl]methanol (14) (1.78 g, 6.4 mmol) in methylene chloride (9 ml), kept at 0° C. The reaction mixture is stirred at 0° C. for 1 hour and then the solvent is evaporated under reduced pressure. The residue is taken up in 30 ml of cyclohexane and stirred for 1 hour. The precipitate formed is filtered and the filtrate concentrated. The residue is purified by flash chromatography on silica gel (cyclohexane/ethyl acetate: 95/5). The title product is obtained in the form of a pale yellow liquid (1.5 g).

$^1$H NMR (CDCl$_3$): δ 0.25 (s, 6H); 1.04 (s, 9H); 4.70 (s, 2H); 6.70 (s, 1H); 6.80 (d, J=7.5 Hz, 1H); 7.07 (t, J=7.7 Hz, 1H); 7.14 (d, J=7.7 Hz, 1H).

Example 15 tert-Butyldimethyl-(2-methylene-2,3-dihydrobenzofuran-7-yloxy)silane (16)

$LiAlH_4$ (1.0M in tetrahydrofuran, 4.5 ml, 4.5 mmol) is added dropwise to a suspension of $CrCl_3$ (1.4 g, 8.85 mmol) in tetrahydrofuran (10 ml), kept at 0° C. and the mixture is stirred for 15 minutes. The solution is then diluted with dimethylformamide (18 ml) and isopropanol (1.35 ml). tert-Butyldimethyl-(2-chloromethylbenzofuran-7-yloxy)silane (15) (1.05 g, 3.54 mmol) in dimethylformamide (15 ml) is added to the solution obtained, kept at 0° C. The mixture is stirred at room temperature for 18 hours and then poured into water and extracted with pentane. The organic phase is dried over $Na_2SO_4$, filtered and concentrated under reduced pressure. A colorless liquid is obtained (0.78 g) which is used in the next step without further purification.

$^1$H NMR (CDCl$_3$): δ 0.21 (s, 6H); 1.00 (s, 9H); 3.89 (s, 2H); 4.26 (d, J=2.0 Hz, 1H); 4.69 (d, J=2.0 Hz, 1H); 7.72 (m, 1H); 7.79 (m, 1H).

Example 16 tert-Butyldimethyl-(2-spirocyclopropane-2,3-dihydrobenzofuran-7-yloxy)silane (17)

A solution of diethylzinc in toluene (1.1M, 6.8 ml, 7.48 mmol) is added to a solution of tert-butyldimethyl-(2-methylene-2,3-dihydrobenzofuran-7-yloxy)silane (16) (0.78 g, 2.97 mmol) in dichloroethane (15 ml) kept at 0° C. After the addition, 1.1 ml of chloroiodomethane (15 mmol) are added and the mixture is stirred at 0° C. for 1 hour and then at 50° C. for 1.5 hours. The mixture is cooled to 0° C. and a saturated aqueous ammonium chloride solution (10 ml) is added. After stirring for 15 minutes, the mixture is diluted with methylene chloride, washed with water and then with a saturated aqueous sodium chloride solution. The organic phase is dried over $Na_2SO_4$, filtered and concentrated under reduced pressure. The residue is purified by flash chromatography on silica gel (cyclohexane/ethyl acetate: 98/2). The title product is obtained in the form of a colorless oil (0.75 g).

$^1$H NMR (CDCl$_3$): δ 0.15 (s, 6H); 0.67 (s, 2H); 0.96 (s, 9H); 1.16 (s, 2H); 3.28 (s, 2H); 6.69 (m, 2H); 6.77 (m, 1H).

Example 17

2-Spirocyclopropane-2,3-dihydrobenzofuran-7-ol (10f)

A solution of tetrabutylammonium fluoride (1.0M in tetrahydrofuran, 3.1 ml, 3.1 mmol) is added to a solution of tert-butyldimethyl-(2-spirocyclopropane-2,3-dihydrobenzofuran-7-yloxy)silane (17) (0.57 g, 2.06 mmol) in 10 ml of tetrahydrofuran at 0° C. The solution is stirred at 0° C. for 2 hours and then poured into water and extracted with ethyl acetate. The organic phase is washed with a saturated aqueous sodium chloride solution, dried over $Na_2SO_4$, filtered and concentrated under reduced pressure. The residue is purified by flash chromatography on silica gel (cyclohexane/ethyl acetate: 80/20). The title product (0.3 g) is obtained in the form of a white solid.

m.p.=85–86° C.; $^1$H NMR (CDCl$_3$): δ 0.71 (t, J=6.4 Hz, 2H); 1.20 (t, J=6.4 Hz, 2H); 3.34 (s, 2H); 4.77 (s, 1H); 6.76 (m, 3H).

Example 18

[2-(2,2-Dimethyl-2,3-dihydrobenzofuran-7-yloxy)ethyl]-(3-cyclopenten-1-ylbenzyl)amine (1a)

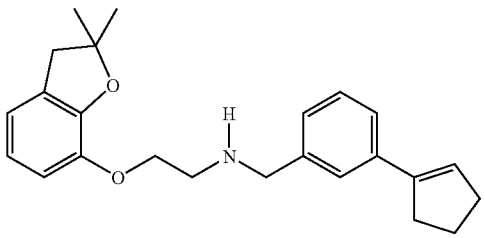

(1a)

1.5 g of magnesium sulfate are added to a solution of 3-cyclopenten-1-ylbenzaldehyde (2a) (0.56 g, 3.26 mmol) and of [2-(2,2-dimethyl-2,3-dihydrobenzofuran-7-yl-oxy)]ethylamine (3a) (0.68 g, 3.26 mmol) in 15 ml of 1,2-dichloroethane and the mixture is heated at 60° C. for 17 hours. The mixture is cooled to room temperature, the solid is filtered and the solvent is evaporated under reduced pressure. The residue is diluted with 15 ml of methanol and then cooled to 0° C. 0.35 g of potassium borohydride (6.52 mmol) is then introduced and the reaction mixture is stirred for 3 hours at 0° C. The mixture is then poured into ice-cold water, extracted with ethyl acetate and washed with a saturated aqueous sodium chloride solution. The combined organic phases are dried over magnesium sulfate, filtered and the solvent is evaporated under reduced pressure. The residue is purified by chromatography on silica gel (methylene chloride/methanol/aqueous ammonia: 98/1.5/0.5). The title product (0.61 g) is isolated in the form of a colorless oil.

$^1$H NMR (CDCl$_3$): δ 1.48 (s, 6H); 2.00 (m, 2H); 2.54 (m, 2H); 2.69 (m, 2H); 3.01 (s, 2H); 3.04 (t, J=5.6 Hz, 2H); 3.85 (s, 2H); 4.18 (t, J=5.6 Hz, 2H); 6.18 (s, 1H); 6.74 (m, 3H); 7.19 (d, J=7.4 Hz, 1H); 7.25 (t, J=8.7 Hz, 1H); 7.32 (d, J=7.6 Hz, 1H); 7.41 (s, 1H)

Fumarate of the title compound:

m.p.=146° C. $^1$H NMR (DMSOd$^6$): δ 1.39 (s, 6H); 1.96 (m, 2H); 2.51 (m, 2H); 2.65 (m, 2H); 2.96 (t, J=5.6 Hz, 2H); 2.99 (s, 2H); 3.91 (s, 2H); 4.11 (t, J=5.6 Hz, 2H); 6.27 (s, 1H); 6.56 (s, 2H); 6.71 (m, 1H); 6.79 (m, 2H); 7.31 (m, 2H); 7.37 (d, J=7.6 Hz, 1H); 7.50 (s, 1H). IR (KBr) ν: 3060, 2967, 1719, 1463 cm$^{-1}$; Elemental analysis for C$_{24}$H$_{29}$NO$_2$.C$_4$H$_4$O$_4$ Theoretical %: C, 70.13; H, 6.94; N, 2.92. Found: C, 69.92; H, 6.93; N, 2.89.

Example 19

[2-(Benzofuran-7-yloxy)ethyl]-(3-cyclopenten-1-ylbenzyl)amine (1c)

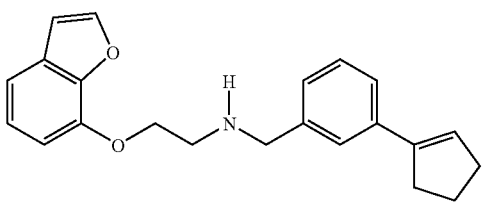

(1c)

By carrying out the procedure as in example 18, but using the 2-(benzofuran-7-yloxy)ethylamine of formula (3c) in place of [2-(2,2-dimethyl-2,3-dihydrobenzofuran-7-yloxy)]ethylamine of formula (3a), the title compound is obtained.

$^1$H NMR (CDCl$_3$): δ 2.04 (m, 2H); 2.53 (m, 2H); 2.70 (m, 2H); 3.12 (t, J=5.2 Hz, 2H); 3.90 (s, 2H); 4.33 (t, J=5.2 Hz, 2H); 6.19 (s, 1H); 6.76 (s, 1H); 6.83 (d, J=7.6 Hz, 1H); 7.13 (t, J=7.8 Hz, 1H); 7.19 (m, 2H); 7.29 (m, 2H); 7.33 (d, J=7.5 Hz, 1H); 7.44 (s, 1H); 7.61 (d, J=2.0 Hz, 1H).

Fumarate of the title product:

m.p.=126° C. $^1$H NMR (DMSOd$^6$): δ 1.95 (m, 2H); 2.49 (m, 2H); 2.64 (m, 2H); 3.04 (t, J=5.6 Hz, 2H); 3.91 (s, 2H); 4.29 (t, J=5.6 Hz, 2H); 6.26 (s, 1H); 6.57 (s, 2H); 6.93 (m, 2H); 7.15 (t, J=7.8 Hz, 1H); 7.26 (m, 3H); 7.36 (d, J=7.2 Hz, 1H); 7.49 (s, 1H); 7.95 (s, 1H); IR (KBr) ν: 3498, 2952, 2842, 1701, 1486 cm$^{-1}$; Elemental analysis for C$_{22}$H$_{23}$NO$_2$.C$_4$H$_4$O$_4$ Theoretical %: C, 69.47; H, 6.05; N, 3.12. Found: C, 69.25; H, 6.08; N, 3.05.

Example 20

[2-(2-Methylbenzofuran-7-yloxy)ethyl]-(3-cyclopenten-1-ylbenzyl)amine (1d)

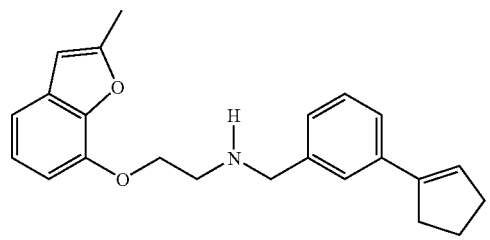

(1d)

By carrying out the procedure as in example 18, but using the 2-(2-methylbenzofuran-7-yloxy)ethylamine of formula (3d) in place of [2-(2,2-dimethyl-2,3-dihydrobenzofuran-7-yloxy)]ethylamine of formula (3a), the title compound is obtained.

$^1$H NMR (CDCl$_3$): δ 2.01 (m, 2H); 2.45 (s, 3H); 2.53 (m, 2H); 2.71 (m, 2H); 3.12 (t, J=5.6 Hz, 2H); 3.89 (s, 2H); 4.32 (t, J=5.6 Hz, 2H); 6.20 (s, 1H); 6.36 (s, 1H); 6.76 (m, 1H); 7.07 (m, 2H); 7.21 (d, J=7.4 Hz, 1H); 7.28 (m, 2H); 7.33 (d, J=7.6 Hz, 1H); 7.43 (s, 1H).

Fumarate of the title product:

m.p.=133° C. $^1$H NMR (DMSOd$_6$): δ 1.96 (m, 2H); 2.43 (s, 3H); 2.49 (m, 2H); 2.67 (m, 2H); 3.02 (t, J=5.6 Hz, 2H); 3.89 (s, 2H); 4.26 (t, J=5.6 Hz, 2H); 6.26 (s, 1H); 6.55 (s, 1H); 6.57 (s, 2H); 6.84 (m, 1H); 7.08 (m, 2H); 7.28 (m, 2H); 7.35 (d, J=7.3 Hz, 1H); 7.49 (s, 1H); IR (KBr) ν: 3421, 3048, 2952, 2846, 1709, 1587 cm$^{-1}$; Elemental analysis for C$_{23}$H$_{25}$NO$_2$.C$_4$H$_4$O$_4$ Theoretical %: C, 69.96; H, 6.31; N, 3.02. Found: C, 70.04; H, 6.30; N, 2.98.

Example 21

[2-(2,3-Dihydrobenzofuran-7-yloxy)ethyl]-(3-cyclopenten-1-ylbenzyl)amine (1e)

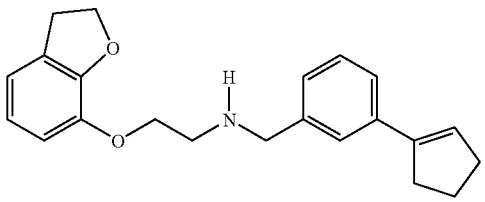

(1e)

By carrying out the procedure as in example 18, but using the 2-(2,3-dihydrobenzofuran-7-yloxy)ethylamine of formula (3e) in place of [2-(2,2-dimethyl-2,3-dihydrobenzofuran-7-yloxy)]ethylamine of formula (3a), the title compound is obtained.

$^1$H NMR (DMSOd$^6$): δ 1.95 (m, 2H); 2.40 (m, 2H); 2.65 (m, 2H); 2.81 (t, J=5.6 Hz, 2H); 3.13 (t, J=8.8 Hz, 2H); 3.74 (s, 2H); 4.03 (t, J=5.6 Hz, 2H); 4.46 (t, J.=8.8 Hz, 2H); 6.25 (s, 1H); 6.79 (m, 3H); 7.27 (m, 3H); 7.42 (s, 1H).

Fumarate of the title product:
m.p.=118° C. $^1$H NMR (DMSOd$^6$): δ 1.92 (m, 2H); 2.49 (m, 2H); 2.65 (m, 2H); 2.93 (t, J=5.6 Hz, 2H); 3.16 (t, J=8.8 Hz, 2H); 3.88 (s, 2H); 4.11 (t, J=5.6 Hz, 2H); 4.50 (t, J=8.8 Hz, 2H); 6.27 (s, 1H); 6.56 (s, 2H); 6.81 (m, 3H); 7.24 (d, J=6.9 Hz, 1H); 7.30 (t, J=7.4 Hz, 1H); 7.36 (d, J=7.3 Hz, 1H); 7.48 (s, 1H); IR (KBr) ν: 3536, 3448, 2949, 2851, 1612, 1466 cm$^{-1}$;

Elemental analysis for $C_{22}H_{25}NO_2 \cdot C_4H_4O_4$ Theoretical %: C, 69.16; H, 6.47; N, 3.10. Found: C, 68.99; H, 6.55; N, 3.32.

Example 22

[2-(2-Spirocyclopropyl-2,3-dihydrobenzofuran-7-yloxy)ethyl]-(3-cyclopenten-1-ylbenzyl)amine (1f)

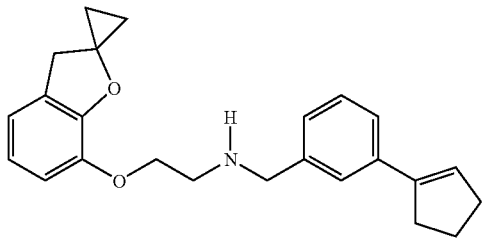

(1f)

By carrying out the procedure as in example 18, but using the 2-(2-spirocyclopropyl-2,3-dihydrobenzofuran-7-yloxy) ethylamine of formula (3f) in place of [2-(2,2-dimethyl-2,3-dihydrobenzofuran-7-yloxy)]ethylamine of formula (3a), the title compound is obtained.

$^1$H NMR (CDCl$_3$): δ 0.69 (t, J=6.4 Hz, 2H); 1.22 (t, J=6.4 Hz, 2H); 1.23 (s, 1H); 2.01 (m, 2H); 2.51 (m, 2H); 2.70 (m, 2H); 3.01 (t, J=5.2 Hz, 2H); 3.31 (s, 2H); 3.84 (s, 2H); 4.17 (t, J=5.2 Hz, 2H); 6.18 (s, 1H); 6.83 (m, 3H); 7.18 (d, J=7.4 Hz, 1H); 7.25 (t, J=7.6 Hz, 1H); 7.31 (d, J=7.6 Hz, 1H); 7.40 (s, 1H).

Maleate of the title product:
m.p.=180° C. $^1$H NMR (DMSOd$^6$): δ 0.78 (t, J=6.4 Hz, 2H); 1.06 (t, J=6.4 Hz, 2H); 1.98 (m, 2H); 2.51 (m, 2H); 2.67 (m, 2H); 3.32 (m, 4H); 4.23 (m, 4H); 6.02 (s, 2H); 6.32 (s, 1H); 6.83 (m, 3H); 7.38 (m, 2H); 7.51 (d, J=7.6 Hz, 1H); IR (KBr) ν: 3454, 2998, 2957, 2841, 1621, 1461 cm$^{-1}$; Elemental analysis for $C_{24}H_{27}NO_2 \cdot C_4H_4O_4$ Theoretical %: C, 70.42; H, 6.54; N, 2.93. Found: C, 70.27; H, 6.59; N, 3.14.

Example 23

[2-(2,2-Dimethyl-2,3-dihydrobenzofuran-7-yl-oxy) ethyl]-[3-(2-fluorocyclopenten-1-yl)benzyl]amine (1g)

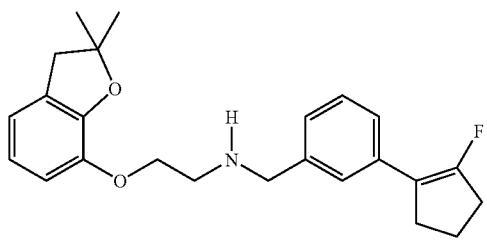

(1g)

By carrying out the procedure as in example 18, but using 3-(2-fluorocyclopenten-1-yl)benzaldehyde of formula (2b) in place of the 3-cyclopenten-1-ylbenzaldehyde of formula (2a), the title compound is obtained.

$^1$H NMR (CDCl$_3$): δ 1.48 (s, 6H); 1.97 (s, 1H); 2.01 (m, 2H); 2.68 (m, 4H); 3.00 (s, 2H); 3.03 (t, J=5.2 Hz, 2H); 3.86 (s, 2H); 4.19 (t, J=5.2 Hz, 2H); 6.78 (m, 3H); 7.21 (d, J=7.5 Hz, 1H); 7.29 (t, J=7.6 Hz, 1H); 7.41 (d, J=7.6 Hz, 1H); 7.44 (s, 1H).

Fumarate of the title product:
m.p.=145° C. $^1$H NMR (DMSOd$^6$): δ 1.39 (s, 6H); 1.95 (m, 2H); 2.67 (m, 4H); 2.94 (t, J=5.6 Hz, 2H); 3.03 (s, 2H); 3.87 (s, 2H); 4.09 (t, J=5.6 Hz, 2H); 6.57 (s, 2H); 6.72 (m, 1H); 6.79 (m, 2H); 7.27 (d, J=7.5 Hz, 1H); 7.34 (m, 2H); 7.47 (s, 1H); IR (KBr) ν: 3426, 2962, 1675, 1463 cm$^{-1}$; Elemental analysis for $C_{24}H_{28}NFO_2 \cdot C_4H_4O_4$ Theoretical %: C, 67.59; H, 6.48; N, 2.82. Found: C, 67.44; H, 6.59; N, 2.88.

Example 24

[2-(2,2-Dimethyl-2,3-dihydrobenzofuran-7-yl-oxy) ethyl]-(5-cyclopenten-1-ylpyridin-3-ylmethyl)amine (1b).

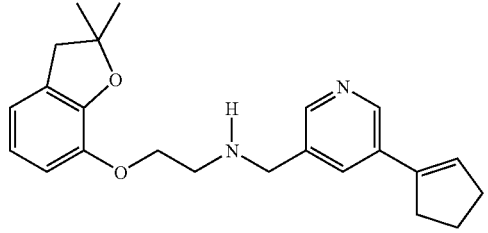

(1b)

By carrying out the procedure as in example 18, but using 5-cyclopenten-1-ylpyridin-3-ylcarboxaldehyde of formula (2c) in place of the 3-cyclopenten-1-ylbenzaldehyde of formula (2a), the title compound is obtained.

$^1$H NMR (CDCl$_3$): δ 1.74 (s, 6H); 2.06 (m, 2H); 2.54 (m, 2H); 2.70 (m, 2H); 3.01 (m, 4H); 3.86 (s, 2H); 4.19 (t, J=5.2 Hz, 2H); 6.28 (s, 1H); 6.75 (m, 3H); 7.71 (s, 1H); 8.49 (s, 1H); 8.57 (s, 1H).

Fumarate of the title product:

m.p.=141° C. $^1$H NMR (DMSOd$^6$): δ 1.39 (s, 6H); 1.98 (m, 2H); 2.51 (m, 2H); 2.69 (m, 2H); 2.92 (t, J=5.6 Hz, 2H); 2.98 (s, 2H); 3.89 (s, 2H); 4.08 (t, J=5.6 Hz, 2H); 6.42 (s, 1H); 6.59 (s, 2H); 6.71 (m, 1H); 6.78 (m, 2H); 7.84 (s, 1H); 8.50 (s, 1H); 8.59 (s, 1H); IR (KBr) v: 3036, 2973, 2847, 1715, 1618, 1491 cm$^{-1}$; Elemental analysis for C$_{23}$H$_{28}$N$_2$O$_2$·C$_4$H$_4$O$_4$ Theoretical %: C, 67.48; H, 6.71; N, 5.83. Found: C, 67.14; H, 6.72; N, 5.79.

Pharmacological Study of the Compounds of the Invention

1—Measurement of the affinity of the compounds of the invention for the D$_2$ receptors.

The affinity in vitro of the compounds of the invention for the receptors of the D$_2$ type was determined by measuring the displacement of ($^3$H) YM-09151-2 (NET-1004 70–87 Ci/mmol) according to the method described in Naunyn-Schimiedeberg's Arch. Pharmacol. Methods, 1985, 329, 333. The pKi values, (pKi=−log Ki), are given in the form of the mean±SEM of at least 3 experiments.

2—Measurement of the affinity of the compounds of the invention for the 5-HT1$_A$ receptors.

The affinity in vitro of the compounds of the invention for the receptors of the 5-HT1$_A$ subtype was determined by measuring the displacement of [$^3$H]8-OH-DPAT (TRK 850; 160–240 Ci/mmol). The study of the binding to the 5-HT1$_A$ receptor is carried out as described by Sleight and Peroutka (Naunyn-Schimiedeberg's Arch. Pharmaco. 1991, 343, 106).

The pKi values, (pKi=−log Ki), are given in the form of the mean±SEM of at least 3 experiments.

3—Evaluation of the antagonist activity of the D$_2$ receptors in vivo.

The test demonstrating the antidopaminergic activity in vivo of the compounds of the invention is based on the inhibition of the behavior induced by methylphenidate, measured in rats, according to the method described in J. Pharmacol. Exp. Ther. 1993, 267, 181.

4—Evaluation of the cataleptigenic effects of the compounds of the invention.

The test which makes it possible to evaluate the propensity of the products of the invention to cause side effects of an extrapyramidal nature is based on their cataleptigenic power, measured in rats, according to the method described in Eur. J. Pharmacol, 1996, 313, 25.

The table below gives, by way of example, the pKi values, measured on the D$_2$ and 5-HT1$_A$ receptors, and the effective doses (ED$_{50}$) obtained after administration of certain products of the invention by the oral route in animals. The properties of the compounds of the invention are compared with those of substances chosen as reference which are used in human clinical medicine, i.e. nemonapride (mixed compound: D$_2$ antagonist and 5-HT1$_A$ agonist), risperidone (atypical antipsychotic) and haloperidol (conventional antipsychotic).

TABLE

| Compound | D$_2$ pKi | 5-HT1$_A$ pKi | Normalization ED$_{50}$ mg/kg | Catalepsy ED$_{50}$ mg/kg |
|---|---|---|---|---|
| 1a | 9.5 | 8.2 | 1.3 | >40 |
| 1f | 9.2 | 8.2 | 0.63 | >40 |
| nemonapride | 9.9 | 8.4 | 1.5 | 5.0 |
| Risperidone | 8.7 | 6.0 | 6.5 | 3.5 |
| haloperidol | 9.0 | 5.8 | 0.46 | 0.92 |

It is evident from this study that the compounds of the invention possess a high affinity for the receptors of the D$_2$ and 5-HT1$_A$ subtypes. The ratio of the pKi values, which is practically identical for the compounds of the invention and nemonapride [pKi(D$_2$)/pKi(%−HT1$_A$) ≅ 1.3], shows that the compounds of the invention and nemonapride have comparable affinity profiles (D$_2$ and 5-HT1$_A$). Risperidone and haloperidol possess, for their part, a good affinity for the D$_2$ receptors, but exhibit only a low affinity for the 5-HT1$_A$ receptors.

The antidopaminergic activities in vivo of the products of the invention and those of the reference compounds are expressed in relatively comparable dose ranges. On the basis of the criterion for normalization of the stereotypisms, the contribution made by a 5-HT1$_A$ activation therefore does not appear in a striking manner. However, we observe that among the compounds of the study, the products having a high affinity for the 5-HT1$_A$ receptors (i.e. 1a, 1f and nemonapride) have a lower propensity to cause catalepsy. This tendency is clearly illustrated by the comparison of the ratios of the cataleptigenic doses (undesirable effect) and those necessary to normalize behavior (desired pharmacological activity); thus, ED$_{50}$(catalepsy)/ED$_{50}$(normalization) >1 in the case of the products 1a, if and nemonapride whereas ED$_{50}$(catalepsy)/ED$_{50}$(normalization)<1 in the case of risperidone and haloperidol. On the basis of the results for catalepsy which are obtained with nemonapride (ED$_{50}$=5 mg/kg), it is surprising that the compounds of the invention (i.e. 1a and 1f) are, for their part, free of any cataleptigenic effects, even in high doses (i.e. 40 mg/kg). It is once again advantageous to compare the ED$_{50}$(catalepsy)/ED$_{50}$(normalization) ratios; thus, whereas this ratio is approximately equal to 3 in the case of nemonapride, it becomes greater than 30 for compounds 1a and 1f. It therefore appears obvious that:

- the antidopaminergic and serotoninergic activities of the compounds of the invention are both expressed in vivo in the dose ranges tested;
- the activities in question cooperate such that their combination confers a significant advantage on the compounds of the invention not only with respect to the products whose mechanism of action is a priori similar (e.g. nemonapride) but also in relation to the atypical antipsychotics (e.g. risperidone) and conventional antipsychotics (e.g. haloperidol).

The compounds of the invention which are capable of behaving as potent and effective dopaminergic antagonists without however causing the side effects characteristic of the dopaminergic antagonists (i.e. catalepsy in animals), even at doses much higher than the pharmacological doses, are thereby potentially useful in the treatment of disorders in which a dopaminergic dysfunction is involved, in particular schizophrenic psychoses.

The administration of the compounds of the invention may be carried out orally, nasally, sublingually, rectally or parenterally. By way of nonlimiting examples of formulation, a preparation of the compounds of the invention is given below. The ingredients and others which are therapeutically acceptable may be introduced in other proportions without modifying the scope of the invention. The terms "active ingredient" used in the example of formulation below refer to a compound of formula (1) or an addition salt or optionally a hydrate of an addition salt of the compound of formula (1) with a pharmaceutically acceptable inorganic acid or organic acid.

Example of Pharmaceutical Composition

Preparation formula for 1000 tablets each containing 10 mg of active ingredient:

| | |
|---|---|
| Active ingredient | 10 g |
| Lactose | 100 g |
| Wheat starch | 10 g |
| Magnesium stearate | 3 g |
| Talc | 3 g |

The invention claimed is:
1. A compound having the formula (1)

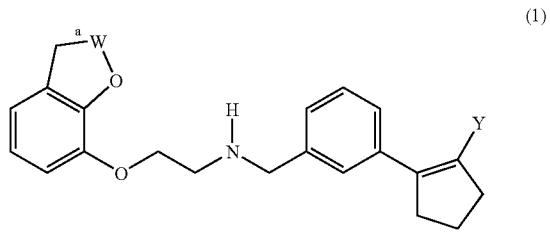

in which
(a) represents a single bond or a double bond;
W represents a CH, $CH_2$, $CHCH_3$, $CCH_3$, or $C(CH_3)_2$ group, a $C(CH_2)_2$ group (i.e. a carbon atom bearing two methylene groups linked together so as to form a spiro-cyclopropane unit) or a $C(CH_2)_3$ group (i.e. a carbon atom bearing two methylene groups linked to another methylene group so as to form a spiro-cyclobutane unit) with the proviso, however, that when (a) is a double bond, then W exclusively represents a CH or $CCH_3$ group, and that when (a) is a single bond, then W exclusively represents a $CH_2$, $CHCH_3$, $C(CH_3)_2$, $C(CH_2)_2$, or $C(CH_2)_3$ group
X is a nitrogen atom; and
Y is a hydrogen atom or a fluorine atom;
or an addition salt or hydrate thereof with a pharmaceutically acceptable inorganic acid or organic acid or organic acid or a tautomeric form, pure enantiomer or mixture of racemic or nonracemic enantiomers thereof.

2. A compound as claimed in claim 1, which is [2-(2,2-dimethyl-2,3-dihydrobenzofuran-7-yloxy)ethyl]-(5-cyclopenten-1-ylpyridine-3-ylmethyl)amin or an addition salt or hydrate of said addition salt with a pharmaceutically acceptable inorganic acid or organic acid or an isomer or tautomer thereof.

3. A pharmaceutical composition comprising, as active ingredient, at least one compound as claimed in claim 1 and an inert pharmaceutical carrier or other pharmaceutically acceptable vehicle.

4. A pharmaceutical composition comprising the compound as claimed in claim 2 and an inert pharmaceutical carrier or other pharmaceutically acceptable vehicle.

5. A method for the treatment of schizophrenia comprising administering to an animal in need of such treatment an effective anti-psychotic amount of a composition as claimed in claim 3.

6. A method for the treatment of schizophrenia comprising administering to an animal in need of such treatment an effective anti-psychotic amount of a composition as claimed in claim 4.

7. A process for the preparation of a compound having the formula (1) as claimed in claim 1, said process comprising reacting a compound having the formula (3) with a compound having the formula (2) according to the reaction scheme:

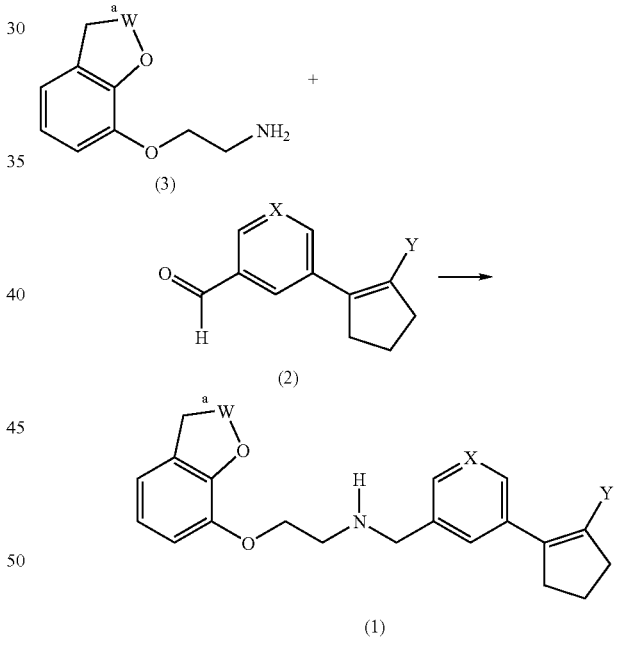

in which (a), W, X and Y are as defined in claim 1.

* * * * *